United States Patent
Zhang et al.

(10) Patent No.: US 10,077,227 B2
(45) Date of Patent: Sep. 18, 2018

(54) METHOD FOR SYNTHESIZING AN ALKENOIC ACID

(71) Applicant: Agency for Science, Technology and Research, Singapore (SG)

(72) Inventors: Yugen Zhang, Singapore (SG); Xiukai Li, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/541,925

(22) PCT Filed: Apr. 15, 2016

(86) PCT No.: PCT/SG2016/050179
§ 371 (c)(1),
(2) Date: Jul. 6, 2017

(87) PCT Pub. No.: WO2006/167726
PCT Pub. Date: Oct. 20, 2016

(65) Prior Publication Data
US 2018/0002267 A1    Jan. 4, 2018

(30) Foreign Application Priority Data
Apr. 15, 2015  (SG) .............................. 10201502962S

(51) Int. Cl.
*C07C 51/25* (2006.01)
*C07C 29/60* (2006.01)
(Continued)

(52) U.S. Cl.
CPC ............. *C07C 51/25* (2013.01); *B01J 23/002* (2013.01); *B01J 23/22* (2013.01); *B01J 23/28* (2013.01);
(Continued)

(58) Field of Classification Search
None
See application file for complete search history.

(56) References Cited

U.S. PATENT DOCUMENTS 9,546,124 B2     1/2017 Lee et al.
2016/0115109 A1*  4/2016 Lee ........................ C07C 33/03
568/876

FOREIGN PATENT DOCUMENTS

JP    2008162907      *  7/2008
WO    WO-2014/209065 A1  12/2014
WO    WO 2014/209068    * 12/2014

OTHER PUBLICATIONS

Bohnke ("Selective Oxidation of Methacrolein towards Methacrylic Acid on Mixed Oxide (Mo, V, W) Catalysts. Part 2. Variation of Catalyst Composition and Comparison with Acrolein Oxidation" Ind. Eng. Chem. Res. 2006, 45, p. 8801-8806).*

(Continued)

*Primary Examiner* — Jafar F Parsa
*Assistant Examiner* — Amy C Bonaparte
(74) *Attorney, Agent, or Firm* — Choate, Hall & Stewart LLP

(57) ABSTRACT

There is provided a method for synthesizing an alkenoic acid, in particular acrylic acid comprising the step of oxidizing an alkenyl alcohol in the presence of a metal oxide catalyst to form the alkenoic acid. The invention further provides a step of deoxydehydrating a polyol, including glycerol to obtain said alkenyl alcohol including an allyl alcohol.

17 Claims, 4 Drawing Sheets

(51) Int. Cl.
- *B01J 23/00* (2006.01)
- *B01J 23/28* (2006.01)
- *B01J 23/30* (2006.01)
- *B01J 37/08* (2006.01)
- *B01J 37/00* (2006.01)
- *B01J 23/22* (2006.01)
- *C07C 57/04* (2006.01)

(52) U.S. Cl.
CPC ........... *B01J 23/30* (2013.01); *B01J 37/0009* (2013.01); *B01J 37/0063* (2013.01); *B01J 37/08* (2013.01); *C07C 29/60* (2013.01); *B01J 2523/00* (2013.01); *B01J 2523/55* (2013.01); *B01J 2523/68* (2013.01); *B01J 2523/69* (2013.01); *C07C 57/04* (2013.01)

(56) References Cited

OTHER PUBLICATIONS

Endres ("The influence of tungsten on structure and activity of Mo—V—W-mixed oxide catalysts for acrolein oxidation" Applied Catalysis A: General 325 (2007) p. 237-243).*
Chieregato ("Multielement Crystalline and Pseudocrystalline Oxides as Efficient Catalysts for the Direct Transformation of Glycerol into Acrylic Acid" ChemSusChem, 2015, 8, p. 398-406).*
Dethlefsen, J.R. and Fristrup, P., Rhenium-Catalyzed Deoxydehydration of Diols and Polyols, ChemSusChem., 8: 767-775 (2015).
International Search Report for PCT/SG2016/050179 (ISA/SG), 5 pages (dated Jun. 7, 2016).
Li, X. and Zhang, Y., Highly Efficient Process for the Conversion of Glycerol to Acrylic Acid via Gas Phase Catalytic Oxidation of an Allyl Alcohol Intermediate, ACS Catal., 6: 143-150 (2016).
Written Opinion for PCT/SG2016/050179 (ISA/SG), 6 pages (dated Jun. 7, 2016).

* cited by examiner

[Fig. 1]
Prior art process:
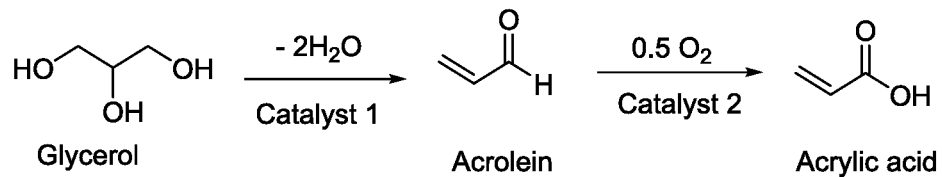
Glycerol → Acrolein → Acrylic acid
[Fig. 2]
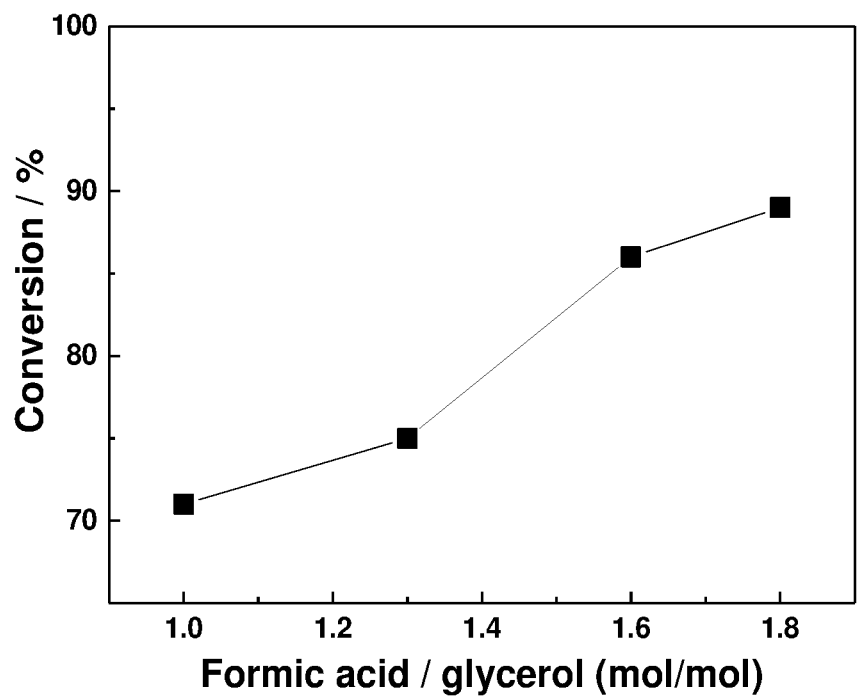

[Fig. 3]
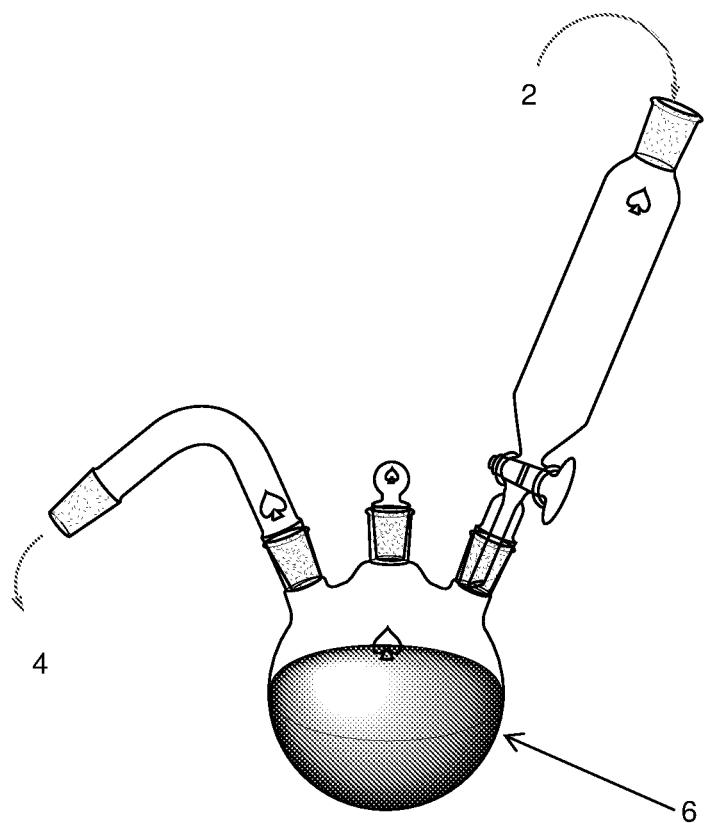

[Fig. 4]
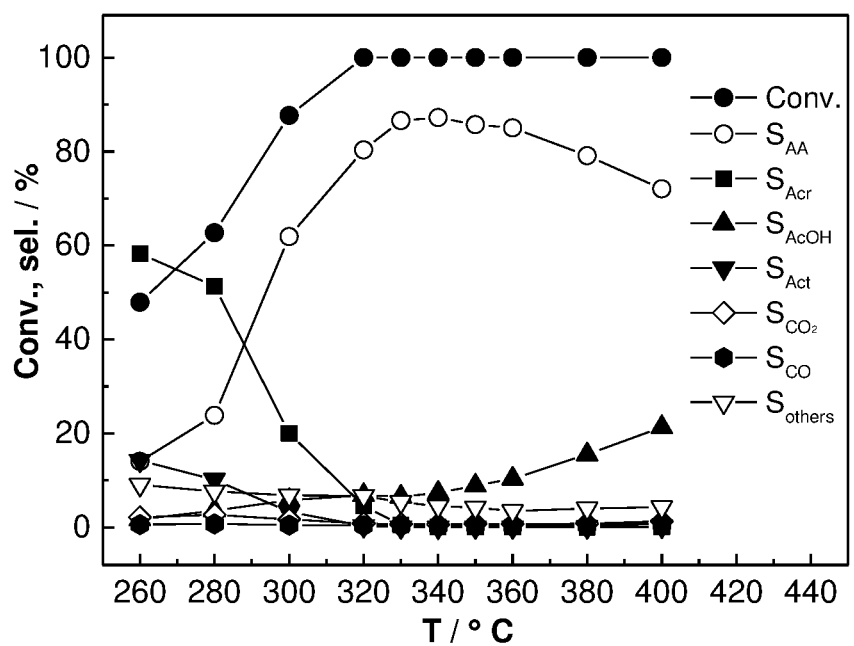

[Fig. 5]
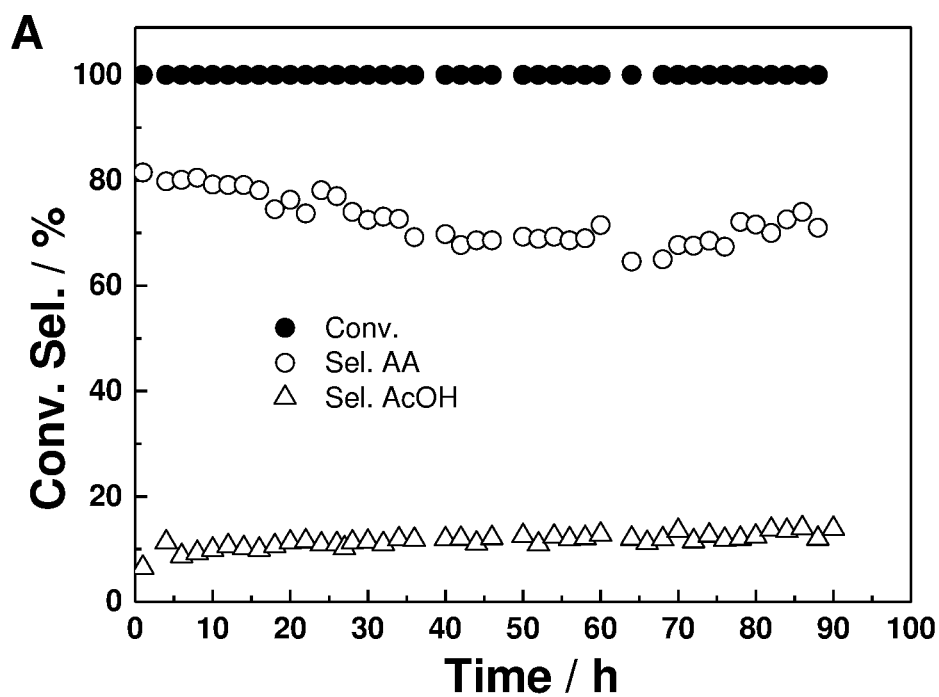
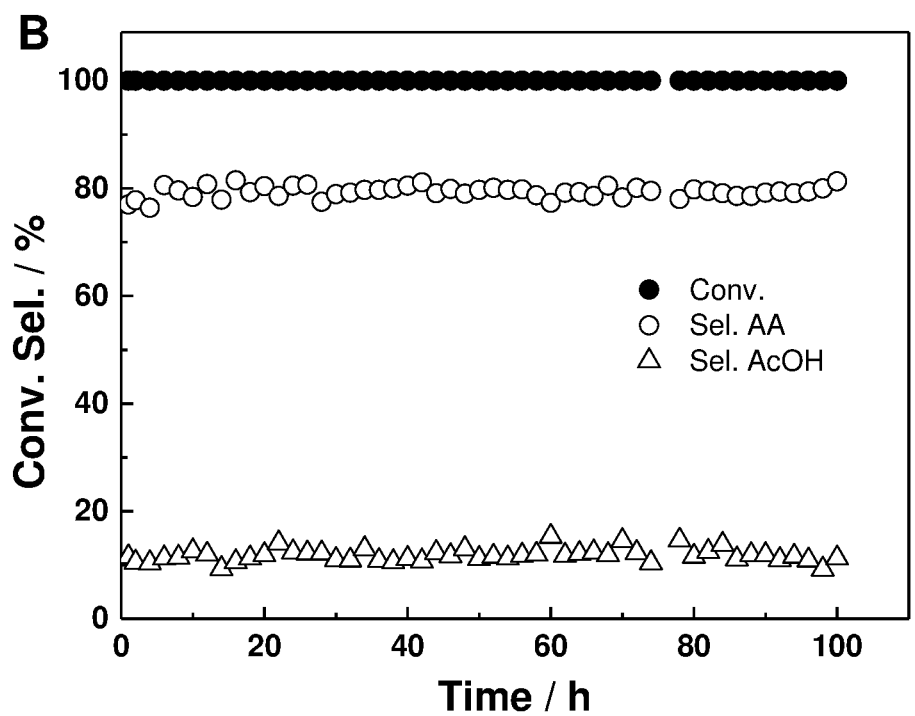

METHOD FOR SYNTHESIZING AN ALKENOIC ACID

CROSS-REFERENCE TO RELATED APPLICATIONS

This patent application is a National Stage Entry of International Patent Application No. PCT/SG2016/050179, filed on Apr. 15, 2016, which claims the benefit of priority from Singapore Patent Application No. 10201502962S filed on Apr. 15, 2015, the contents of each of which are hereby incorporated by reference in their entirety for all purposes herein.

TECHNICAL FIELD

The present invention generally relates to a method for synthesizing an alkenoic acid. The present invention also relates to a method for synthesizing an alkenoic acid from a polyol.

BACKGROUND ART

In view of the growing emphasis on renewable energy, increasing amount of biodiesel is produced as an alternative fuel. Biodiesel production through triglyceride transesterification generates about 10 wt % of glycerol as the main byproduct. The growing biodiesel production will lead to large surpluses of glycerol and will impact the current glycerol market notably. It was expected that approximately 37 billion gallons of biodiesel will be produced by 2016, and therefore approximately 4 billion gallons of crude glycerol will be generated. With the expansion of biodiesel production, the prices for both refined glycerol and crude glycerol have plummeted to less than half of that few years ago and will decrease further. It is imperative to find more uses for the over supplied glycerol, which will be of great importance for the biodiesel economy.

Potentially, the bio-generated glycerol can serve as a platform chemical for the synthesis of value-added products. One such product is acrylic acid (AA), which can be industrially produced from the gas phase oxidation of crude oil-based propene and is used primarily for the large volume production of polyacrylates. The large market demand makes acrylic acid one of the most sought after chemicals from biomass resources. The most known way to produce acrylic acid from glycerol is a two-step tandem reaction (FIG. 1). Glycerol is first dehydrated to acrolein over an acid catalyst, and then oxidized to acrylic acid in the second step. Although up to 90% acrolein yield could be achieved from glycerol dehydration in the first step, most of the acid catalysts suffer from fast deactivation due to heavy coke deposition which is inevitably caused by the acidic nature of the catalysts and the high reaction temperature. There have also been reports on direct oxidehydration conversion of glycerol to acrylic acid over bifunctional catalysts. However, the selectivity to acrylic acid is normally lower than 50%, with catalyst deactivation as a severe problem. Thus, from a practical application point of view, the catalyst stability remains a critical issue for the current dehydration-oxidation route or the direct oxidehydration route.

There is a need to provide a method for synthesizing an alkenoic acid such as acrylic acid that overcomes, or at least ameliorates, one or more of the disadvantages described above.

SUMMARY OF INVENTION

According to a first aspect, there is provided a method for synthesizing an alkenoic acid comprising the step of oxidizing an alkenyl alcohol in the presence of a metal oxide catalyst to form said alkenoic acid.

According to a second aspect, there is provided a method for synthesizing an alkenoic acid from a polyol comprising the steps of (a) deoxydehydrating the polyol in the presence of a carboxylic acid to form an alkenyl alcohol; and (b) oxidizing the alkenyl alcohol in the presence of a metal oxide catalyst to form the alkenoic acid.

Advantageously, the above methods may be highly selective, may be stable with high conversion rate of the alkenyl alcohol and/or may form the alkenoic acid with high yields.

Advantageously, the metal oxide catalyst may not suffer from catalyst deactivation that may be experienced in a conventional process (such as shown in FIG. 1).

Definitions

The following words and terms used herein shall have the meaning indicated:

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a method for synthesizing an alkenoic acid will now be disclosed.

The method for synthesizing an alkenoic acid may comprise the step of oxidizing an alkenyl alcohol in the presence of a metal oxide catalyst to form the alkenoic acid.

The alkenyl alcohol may be derived from deoxydehydrating a polyol. The deoxydehydration of the polyol to the alkenyl alcohol may be undertaken in the absence of a catalyst.

The polyol may be a compound having two, three, four, five or six hydroxyl groups. The polyol may be a straight- or branched-chain polyol. The polyol may be a diol, triol, tetraol, pentol or hexol. The polyol may be glycerol, 2-methyl-1,2,3-propanetriol,1,2,3-butanetriol, 2-methyl-1,2,3-butanetriol, 2-methyl-1,2,3,4-butanetetraol, 1,2,3-pentanetriol, 1,2,3-hexanetriol, xylitol, sorbitol, arabinitol, ribitol, mannitol, galactitol, iditol, erythritol, threitol or a mixture thereof. The polyol may be glycerol or erythritol.

The alkenyl alcohol may be a straight- or branched-chain alcohol having from 2 to 12 carbon atoms. The alkenyl alcohol may be a vinyl alcohol or a 2-alkenyl alcohol having from three to 12 carbon atoms. Where the alkenyl alcohol is a 2-alkenyl alcohol, the 2-alkenyl alcohol may be selected from the group consisting of allyl alcohol, 2-buten-1-ol, 2-hexen-1-ol, 2-penten-1,4,5-triol, 2,4-hexadien-1,6-diol, 2-hexene-1,4,5,6-tetraol, 2-methyl-2-butenol, 2-butene-1,4-diol, 2-methyl-2-butene-1,4-diol, methallyl alcohol, 2-chloroallyl alcohol, ethallyl alcohol and crotyl alcohol. The alkene may be in the cis- or trans-conformation.

The alkenoic acid may be linear or branched monocarboxylic or dicarboxylic acids. The alkenoic acid may have three to 12 carbon atoms or three to six carbon atoms. An alkenoic acid may encompass an allylic acid. In the alkenoic acid or the allylic acid, the C=C double bond may be present between the second and third carbon atoms of the main carbon chain when considering the carbon atom of the carboxylic/carboxylate functional group as the first carbon. The alkenoic acid may be selected from the group consisting of acrylic acid, methacrylic acid, maleic acid, fumaric acid, 4-hydroxy-2-butenoic acid, 2-hydroxy-3-pentendioic acid, 4,5-dihydroxy-2-pentenoic acid, 2,5-dihydroxy-3-pentenoic acid, crotonic acid, citraconic acid, mesaconic acid, angelic acid, tiglic acid, 4,5,6-trihydroxy-2-hexenoic acid, 2,3,5-trihydroxy-4-hexenoic acid and 4,5-dihydroxy-2-hexenedionic acid. The alkene may be in the cis- or trans-conformation. Particularly, the alkenoic acid may be an allylic acid. Particularly, where the 2-alkenyl alcohol precursor is a diol, the alkenoic acid or allylic acid formed may be a mono-acid, a di-acid or a mixture thereof.

The metal oxide catalyst may comprise at least one metal. The at least one metal may be at least one transition metal. The at least one transition metal may be selected from the group consisting of molybdenum, vanadium, titanium, chromium, manganese, iron, cobalt, nickel, copper, zinc, yttrium, zirconium, niobium, ruthenium, rhodium, lanthanum, cerium, tantalum, tungsten, rhenium and combinations thereof. The metal oxide catalyst may have 1, 2, 3, 4 or 5 metals therein.

The metal oxide catalyst may have the formula $Mo_xV_yA_mB_nO_d$ where A and B independently refers to a transition metal and may be optional, x refers to a number between 1 to 10 (both limits inclusive), y refers to a number between 0.05 to 10 (both limits inclusive), m refers to a number between 0 to 10 (both limits inclusive), n refers to a number between 0 to 10 (both limits inclusive) and d is calculated based on the amount of the metals present in the formula in which $d=3x+2y+3m+3n$. It is to be noted that the ranges recited above also include the sub-ranges that fall within the broader range and this disclosure is to be interpreted as including all of the sub-ranges (even if not explicitly provided) encompassed by the broader ranges above as well as discrete values that fall within the range, the discrete values being a whole number or a fraction.

The metal oxide catalyst may be a supported catalyst or an unsupported catalyst. When the metal oxide catalyst is a supported catalyst, the support material may be porous or nonporous materials such as silica, aluminium oxide, aluminate or titanium oxide. The support material used may be SBA-15, calcium aluminate, magnesium aluminate, zeolite, ceramics. The BET surface area of the metal oxide catalyst is not particularly limited and depends on the type of metal oxide catalyst used. The BET surface area of the metal oxide catalyst may range from about 5 $m^2/g$ to about 400 $m^2/g$.

The amount of metal oxide catalyst used may be in the range of about 10 mg to about 500 mg, about 10 mg to about 50 mg, about 10 mg to about 100 mg, about 10 mg to about 150 mg, about 10 mg to about 200 mg, about 10 mg to about 250 mg, about 10 mg to about 300 mg, about 10 mg to about 350 mg, about 10 mg to about 400 mg, about 10 mg to about 450 mg, about 50 mg to about 500 mg, about 100 mg to about 500 mg, about 150 mg to about 500 mg, about 200 mg to about 500 mg, about 250 mg to about 500 mg, about 300 mg to about 500 mg, about 350 mg to about 500 mg, about 400 mg to about 500 mg, about 450 mg to about 500 mg, or about 100 mg to about 200 mg.

The oxidizing step may be undertaken at a temperature in the range of about 200° C. to about 400° C., about 200° C. to about 250° C., about 200° C. to about 300° C., about 200° C. to about 350° C., about 250° C. to about 400° C., about 300° C. to about 400° C., about 350° C. to about 400° C., about 300° C. to about 350° C., or about 300° C. to about 400° C. The oxidizing temperature may be increased to at least about 320° C. or at least about 340° C. to ensure a higher alkenyl alcohol conversion and/or to increase the selectivity of the alkenoic acid. By having a higher oxidizing temperature, this may help to facilitate the oxidation of an intermediary unsaturated aldehyde to form the alkenoic acid. Where the alkenoic acid is acrylic acid, the intermediary unsaturated aldehyde may be acrolein. At a temperature of 340° C., for selected catalysts, substantially 100% conversion of alkenyl alcohol can be obtained with at least 80% alkenoic acid selectivity.

The oxygen content in the oxidizing step may be in the range of about 5% to about 20%, about 5% to about 10%, about 5% to about 15%, about 10% to about 20%, or about 15% to about 20%.

Hence, the alkenyl alcohol conversion and/or alkenoic acid selectivity may be increased by one or more of the following: 1) increasing the amount of metal oxide catalyst used; 2) increasing the oxygen content in the oxidizing step; 3) increasing the oxidizing temperature while avoiding over oxidization; and/or 4) using supported catalysts.

The metal oxide catalyst may be substantially stable for prolonged periods of time. The metal oxide catalyst may be used for more than 20 hours, 30 hours, 40 hours, 50 hours, 60 hours, 70 hours, 80 hours, 90 hours or 100 hours while maintaining the alkenoic acid selectivity and/or alkenyl alcohol conversion. Accordingly, the metal oxide catalyst may not suffer from catalyst deactivation that may be experienced with a conventional process (such as depicted in FIG. 1).

The oxidizing step may be undertaken in a fixed-bed gas-phase system.

The deoxydehydrating step may be undertaken in a liquid phase system. The polyol may be deoxydehydrated in the presence of a carboxylic acid such as formic acid to form the alkenyl alcohol. The polyol may be heated with the carboxylic acid under ambient pressure to form the alkenyl alcohol which can be collected by condensation. The reaction temperature may be in the range of about 200° C. to about 280° C., about 235° C., any temperature or temperature ranges falling within this range. The reaction may be undertaken in an inert gas atmosphere (such as nitrogen or helium) or in air. The molar ratio of the carboxylic acid to polyol may be in the range of about 1:1 to about 3.0:1, about 1.8:1, or any other molar ratios falling within this range. The polyol conversion may be at least about 90%, 91%, 92%, 93%, 94%, 95%, 96%, 97%, 98% or 99%. The yield of the alkenyl alcohol may be at least about 90%, 91%, 92%, 93%, 94%, 95%, 96%, 97%, 98% or 99%. The reaction may be fast. The reaction may be performed in a continuous or non-continuous system. Advantageously, the reaction may be clean and no other side product besides water may be formed. More advantageously, the presence of impurities such as water and methanol may not affect the reaction efficiency.

Hence, the method of synthesizing the alkenoic acid may be highly selective, stable with high conversion rate of the alkenyl alcohol and may form the alkenoic acid with high yields.

There is also provided a method for synthesizing an alkenoic acid from a polyol comprising the steps of: (a) deoxydehydrating the polyol in the presence of a carboxylic acid to form an alkenyl alcohol; and (b) oxidizing the alkenyl alcohol in the presence of a metal oxide catalyst to form the alkenoic acid.

The above process is depicted in Scheme 1 below in which the polyol is glycerol, the carboxylic acid is formic acid, the alkenyl alcohol is allyl alcohol and the alkenoic acid is acrylic acid.

Scheme 1

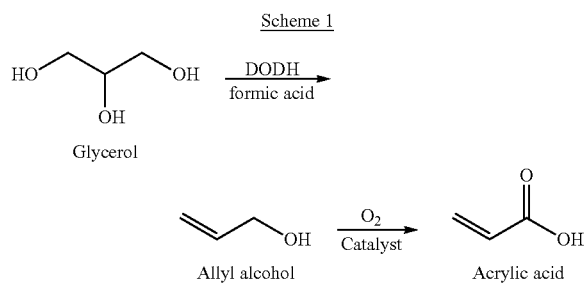

According to Scheme 1 above, glycerol is deoxydehydrated (DODH) by formic acid to allyl alcohol in a batch or continuous flow reaction. Subsequently, allyl alcohol is oxidized to acrylic acid in fixed-bed gas-phase system. The first step reaction is non-catalytic but very efficient and highly productive. Almost quantitative yield of allyl alcohol can be obtained in a short time. It is noteworthy that formic acid is a cheap and green chemical that can be produced from biomass or carbon dioxide. In the second step, supported and unsupported multiple metal oxide catalysts were fabricated for this transformation, and good activity as well as selectivity to acrylic acid was achieved. The metal catalysts for the second step were highly stable on stream under the reaction conditions.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 is a scheme showing a conventional process of forming acrylic acid from glycerol (prior art).

FIG. 2 is a graph showing the conversion of glycerol as a function of molar ratio of formic acid to glycerol. Glycerol 18.2 g (0.2 mol), reaction temperature 235° C., reaction time 2 hours and conversions were determined by High Performance Liquid Chromatography (HPLC).

FIG. 3 is a schematic diagram showing a continuous reaction setup for the formic acid mediated deoxydehydration of glycerol to allyl alcohol.

FIG. 4 is a graph showing the temperature dependence of allyl alcohol oxidation over an experimental catalyst (identified in the examples as catalyst 2#). Reactions conditions were 200 mg, 35 to 60 mesh (catalyst), 20 wt % of allyl alcohol in water at 0.5 ml/h (feed) and 10% $O_2$/He, 20 ml/minute (carrier gas). The weight hourly space velocity (WHSV) was 0.5 g/(g h).

FIG. 5 is a series of graphs showing the time on stream tests for allyl alcohol oxidation over (A) a first experimental catalyst (identified in the examples as catalyst 2#) and (B) a second experimental catalyst (identified in the examples as catalyst 8#). Reactions conditions were 200 mg, 35 to 60 mesh (catalyst), 20 wt % of allyl alcohol in water at 0.5 ml/h (feed) and 10% $O_2$/He, 20 ml/minute (carrier gas). The weight hourly space velocity (WHSV) was 0.5 g/(g h).

EXAMPLES

Non-limiting examples of the invention will be further described in greater detail by reference to specific Examples, which should not be construed as in any way limiting the scope of the invention.

Example 1—Production of Allyl Alcohol

All starting materials were commercially available and were used as received, unless otherwise indicated. Formic acid (99%), glycerol (99%), ammonium monovanadate (99%), and ammonium heptamolybdate (99%) were purchased from Merck Millipore of Massachusetts of the United States of America Ammonium metatungstate (99%) was purchased from Fluka (under Sigma-Aldrich of Missouri of the United States of America).

The process of Scheme 1 was used to form acrylic acid. In a typical condition for the first step of Scheme 1, glycerol was heated with formic acid at 235° C. under ambient atmosphere, and allyl alcohol was collected by condensation. The reaction was very fast and the product was observed immediately when the reaction temperature reached 235° C. The reaction was clean and there was no other side products collected besides water. The conversion of glycerol depended on the amount of formic acid added to the reaction (FIG. 2). At a formic acid to glycerol molar ratio of 1.8:1, 90% glycerol was converted (allyl alcohol yield 89%) in 2 hours. Around 20 to 40% of unreacted formic acid was also collected together with the product. As the formic acid was added in 3 portions, the reaction was almost complete in about 6 hours (including 2 hours interim cooling down and heating up), and allyl alcohol was collected at 97% yield (Entries 1 and 2, Table 1). A gas flow can facilitate the distillation, and there was no difference for nitrogen or air. Moisture and methanol were the main potential impurities in crude glycerol; however, they did not affect the current deoxydehydration reaction even at 20 wt % content (Entries 3 and 4, Table 1). More formic acid was recovered when 20 wt % water was presented (Entry 3, Table 1).

TABLE 1

| Entry | Glycerol | Atmosphere | Conv.$_{gly}$ (%)[c] | Yield (%) | Formic acid recovered (%) |
|---|---|---|---|---|---|
| 1[a] | 100% | $N_2$ | 98 | 97 | 23 |
| 2[a] | 100% | Air | 99 | 98 | 27 |
| 3[a] | 80 wt % in $H_2O$ | $N_2$ | 98 | 97 | 33 |
| 4[a] | 80 wt % in MeOH | $N_2$ | 99 | 98 | 27 |
| 5[b] | 100% | $N_2$ | 99 | 99 | 34 |

Deoxydehydration of glycerol by formic acid. Reaction conditions: glycerol 18.4 g (0.2 mol), formic acid 16.5 g (0.36 mol), 235° C.
[a]Formic acid was added in 3 portions (11.9, 2.3, and 2.3 g). Reaction time: 6 hours.
[b]Continuous reaction. A mixture of glycerol (18.4 g, 0.2 mol) and formic acid (16.5 g, 0.36 mol) was added continuously to the reactor. Reaction time: 2 hours.
[c]Yield and conversion were determined by HPLC.

As the reaction was fast, the continuous reaction model was also tried (FIG. 3, Entry 5, Table 1). Under steady state, a mixture of glycerol (18.4 g, 0.2 mol) and formic acid (16.5 g, 0.36 mol) at a glycerol:formic acid ratio of 1:1.8 (2) was added continuously to a 50 ml flask (heated at 235° C., containing glycerol and formic acid at the same molar ratio) (6) in around 2 hours, and 11.5 g of allyl alcohol (99% yield) (4) was collected together with 5.6 g of unreacted formic acid. This example demonstrates that the continuous production of allyl alcohol from glycerol is feasible and that the productivity is excellent.

The allyl alcohol obtained was then oxidized to acrylic acid in a series of examples below.

Example 2—Effect of Catalyst on Production of Acrylic Acid

Mo and V based multiple metal oxide catalysts with formula $Mo_xN_yA_mB_nO_\delta$ were used for the further oxidation of allyl alcohol to acrylic acid in fixed-bed gas-phase system. Table 2 lists the samples and their surface area ($S_{BET}$). Catalysts 1# to 6# were unsupported catalysts while catalysts 7# to 9# were supported catalysts, in which the support material is SBA-15 (a mesoporous silica material). The unsupported Mo—V—W—O catalysts were prepared by decomposing the ammonium salts of the metal precursors. Stoichiometric amounts of ammonium monovanadate, ammonium heptamolybdate, and ammonium metatungstate were dissolved in deionised water and then evaporated to dryness. The combination was calcined at 275° C. for 4 hours in air and then at 325° C. for 4 hours in a helium environment. The powder sample was pressed into pellets, crushed and sieved using a 35 to 60 mesh before activity evaluation. For the preparation of the supported catalyst, an aqueous solution containing calculated amounts of vanadium, molybdenum, and tungsten precursors was impregnated onto SBA-15 (purchased from Sigma-Aldrich) under stirring at room temperature. The material was dried at 100° C. overnight to remove solvent before calcination at 275° C. for 4 hours in air and then at 325° C. for 4 hours in a helium environment.

TABLE 2

| Catalyst | Type of catalyst | $S_{BET}$ ($m^2 g^{-1}$) |
|---|---|---|
| 1# | $Mo_8V_2O_\delta$ | 8.9 |
| 2# | $Mo_8V_2WO_\delta$ | 12.4 |
| 3# | $Mo_8V_2W_2O_\delta$ | 9.9 |
| 4# | $Mo_9V_3O_\delta$ | 8.2 |
| 5# | $Mo_9V_3WO_\delta$ | 10.1 |
| 6# | $Mo_9V_3W_2O_\delta$ | 10.5 |
| 7# | 60% $Mo_8V_2WO_\delta$/SBA-15 | 187.3 |
| 8# | 40% $Mo_8V_2WO_\delta$/SBA-15 | 272.9 |
| 9# | 20% $Mo_8V_2WO_\delta$/SBA-15 | 329.7 |

Table 3 shows the results of allyl alcohol oxidation over the catalysts. Over 1# and 4# catalysts, acrolein was dominant in the products when the reaction temperature was below 320° C. Other products are acrylic acid, acetaldehyde, acetic acid, and carbon oxides. When the reaction temperature was increased, acrolein was consecutively oxidized to acrylic acid, however the selectivity to acetic acid and the total oxidized products (CO, $CO_2$) was also increased. Over the 2# and 5# catalysts, full allyl alcohol conversion and selectivity to acrylic acid of about 87% and 86% respectively was achieved at a reaction temperature of 340° C.

TABLE 3

| Cat. | T [° C.] | Conv. [%] | Selectivity [%] | | | | |
|---|---|---|---|---|---|---|---|
| | | | Acr | AcOH | AA | CO | $CO_2$ |
| 1# | 300 | 80.5 | 75.2 | 0.8 | 1.4 | 1.7 | 4.0 |
| | 340 | 100.0 | 57.2 | 7.4 | 16.9 | 7.6 | 8.6 |
| 2# | 300 | 87.7 | 20.0 | 5.8 | 61.9 | 0.5 | 1.7 |
| | 340 | 100.0 | 0.1 | 7.3 | 87.2 | 0.3 | 0.6 |
| 3# | 300 | 75.3 | 62.8 | 2.6 | 13.4 | 1.4 | 3.9 |
| | 340 | 100.0 | 17.8 | 8.2 | 61.1 | 3.7 | 6.2 |
| 4# | 300 | 88.1 | 81.1 | 0.4 | 1.5 | 2.0 | 4.6 |
| | 340 | 100.0 | 26.0 | 6.4 | 47.1 | 7.8 | 8.9 |
| 5# | 300 | 90.4 | 37.5 | 2.8 | 42.1 | 1.1 | 2.9 |
| | 340 | 100.0 | 0.5 | 6.0 | 86.2 | 1.2 | 2.2 |
| 6# | 300 | 100.0 | 56.8 | 2.1 | 18.8 | 3.7 | 7.4 |
| | 340 | 100.0 | 0.2 | 10.1 | 62.4 | 10.3 | 14.2 |

Reaction conditions: catalyst, 200 mg, 35~60 mesh; feed, 20 wt % allyl alcohol in $H_2O$, 0.5 ml $h^{-1}$; carrier gas, 10% $O_2$/He, 20 ml $min^{-1}$.
Acr: acrolein.
AA: acrylic acid.
AcOH: acetic acid.
WHSV = 0.5 g/(gh).

Example 3—Effect of Contact Time and Space Velocity of Catalyst

The contact time and space velocity of the catalysts were studied by varying the amount of catalyst loading for the best performed 2# catalyst (Table 4). At lower reaction temperature (e.g. 280° C.), the conversion of allyl alcohol increased with increasing amount of catalyst loaded. When 100 mg of catalyst was loaded, only 33% allyl alcohol conversion but more than 90% acrolein selectivity were observed at 280° C. Both conversion and the selectivity to acrylic acid were improved when the amount of catalyst was increased to 200 mg, and 87% acrylic acid yield was obtained at 340° C. Further increase in the amount of catalyst to 300 mg led to more acetic acid and carbon oxides being produced due to over oxidization. Thus, it is possible to selectively synthesize acrolein or acrylic acid by controlling the reaction temperature and the amount of catalyst or space velocity.

TABLE 4

| Cat. [mg] | Contact time [s] | WHSV [g/(gh)] | T [° C.] | Conv. [%] | Selectivity [%] | | | | |
|---|---|---|---|---|---|---|---|---|---|
| | | | | | Acr | AcOH | AA | CO | $CO_2$ |
| 100 | 0.27 | 1.00 | 280 | 33.4 | 91.0 | 0.0 | 0.0 | 0.7 | 2.0 |
| | | | 400 | 100 | 19.4 | 4.7 | 70.7 | 1.0 | 2.5 |
| 200 | 0.54 | 0.50 | 280 | 62.7 | 51.4 | 3.6 | 23.9 | 0.7 | 2.7 |
| | | | 340 | 100.0 | 0.1 | 7.3 | 87.2 | 0.3 | 0.6 |
| 300 | 0.81 | 0.33 | 280 | 93.3 | 70.6 | 0.6 | 3.1 | 1.9 | 3.7 |
| | | | 340 | 100 | 3.3 | 8.4 | 74.3 | 4.4 | 7.0 |

Reaction conditions: feed, 20 wt % allyl alcohol in $H_2O$, 0.5 ml $h^{-1}$; carrier gas, 10% $O_2$/He 20 ml $min^{-1}$.
Acr: acrolein.
AA: acrylic acid.
AcOH: acetic acid.

Example 4—Effect of Oxygen Content

The oxygen content in the carrier gas was further investigated for the 2# catalyst (Table 5). The conversion of allyl alcohol generally increased with increasing oxygen content. When 5% oxygen was used as the carrier gas, about 81% selectivity to acrylic acid was achieved at 340° C. while the selectivity to the total oxidized products (CO and $CO_2$) was less than 1%. Increasing the oxygen content to 10% gave about 87% yield of acrylic acid at 340° C. Further increasing the oxygen content to 20% led to lower selectivity to acrylic acid. Thus, the oxygen content from 5% to 10% is preferable for the current oxidation reaction.

TABLE 5

| $O_2$ [%] | T [° C.] | Conv. [%] | Selectivity [%] | | | | |
|---|---|---|---|---|---|---|---|
| | | | Acr | AcOH | AA | CO | $CO_2$ |
| 5% | 300 | 58.7 | 20.2 | 6.5 | 58.6 | 0.3 | 1.1 |
| | 340 | 99.3 | 6.0 | 5.4 | 81.5 | 0.2 | 0.5 |
| 10% | 300 | 87.7 | 20.0 | 5.8 | 61.9 | 0.5 | 1.7 |
| | 340 | 100.0 | 0.1 | 7.3 | 87.2 | 0.3 | 0.6 |
| 20% | 300 | 99.0 | 1.2 | 5.7 | 75.3 | 1.5 | 4.4 |
| | 340 | 100.0 | 0.4 | 8.7 | 78.3 | 4.6 | 6.4 |

Reaction conditions: 2# catalyst, 200 mg, 35~60 mesh; feed, 20 wt % allyl alcohol in $H_2O$, 0.5 ml $h^{-1}$; carrier gas x % $O_2$/He 20 ml $min^{-1}$.
Acr: acrolein.
AA: acrylic acid.
AcOH: acetic acid.
WHSV = 0.5 g/(g h).

Example 5—Effect of Temperature

The temperature dependence of the reaction performance of 2# is shown in FIG. 4. The allyl alcohol conversion increased monotonously at elevated temperatures in the 240 to 320° C. region, and full conversion was achieved at a temperature above 320° C. Acrolein is the key intermediate to acrylic acid. The selectivity to acrolein decreased rapidly with the temperature rise, indicating that acrolein was quickly oxidized at higher temperature. In contrast, the selectivity to acrylic acid increased rapidly with the temperature rise, reaching a maximum value of 86.3% at 340° C. Further increase in the temperature led to decreased selectivity to acrylic acid due to over oxidization, as reflected by the increasing amount of acetic acid, CO, and $CO_2$. The selectivity to acetic acid, CO, and $CO_2$ were lower than 10% in the whole temperature range. Acetaldehyde was observed as the main side product at temperature below 320° C., while the formation of acetaldehyde was notably reduced as the temperature increased.

Example 6—Effect of Supported Catalysts

The supported catalysts were evaluated under optimized reaction conditions and the results are listed in Table 6. In contrast to the 87.7% allyl alcohol conversion over the unsupported 2# catalyst at 300° C., full conversion was achieved over all the supported catalysts at the same reaction temperature, indicating much higher activity of the supported catalysts. Over the catalysts 7# and 8# catalysts, greater than 82% acrylic acid yields were observed at reaction temperatures above 340° C. It was also noted that higher reaction temperature did not affect the selectivity to acrylic acid over the supported catalysts. When the reaction temperature was raised from 340° C. to 380° C., the selectivity to acrylic acid for 7# and 8# catalysts was kept above 82%, while it dropped from 86% to 72% for unsupported 2# (data not shown).

TABLE 6

| Cat. | T [° C.] | Conv. [%] | Selectivity | | | | |
|---|---|---|---|---|---|---|---|
| | | | Acr | AcOH | AA | CO | $CO_2$ |
| 2# | 300 | 87.7 | 20.0 | 5.8 | 61.9 | 0.5 | 1.7 |
| | 340 | 100.0 | 0.1 | 7.3 | 87.2 | 0.3 | 0.6 |
| 7# | 300 | 100.0 | 29.7 | 22.2 | 25.5 | 2.9 | 4.3 |
| | 340 | 100.0 | 0.4 | 9.9 | 85.2 | 1.7 | 2.1 |
| 8# | 300 | 100.0 | 6.3 | 22.3 | 50.3 | 2.9 | 5.0 |
| | 340 | 100.0 | 1.0 | 10.9 | 82.8 | 1.1 | 1.9 |
| 9# | 300 | 100.0 | 9.6 | 15.2 | 51.6 | 2.7 | 4.9 |
| | 340 | 100.0 | 4.9 | 11.2 | 61.8 | 2.0 | 4.8 |

Reaction conditions: catalyst 200 mg, 35~60 mesh; feed, 20 wt % allyl alcohol in $H_2O$, 0.5 ml $h^{-1}$; carrier gas, 10% $O_2$/He, 20 ml $min^{-1}$.
Acr: acrolein.
AA: acrylic acid.
AcOH: acetic acid.
WHSV = 0.5 g/(g h).

Example 7—Catalytic Performance of Catalysts

The catalytic performance of catalysts under the optimal reaction conditions were further studied as a function of time on stream (FIG. 5). The complete conversion of allyl alcohol was kept for more than 90 hours over both 2# and 8#. For the 2# catalyst, the selectivity to acrylic acid decreased from 80% to 70% in the initial 30 hours, and then stabilized at around 70% till 90 hours on stream; meanwhile, the selectivity to acetic acid increased from 8% to 20%. The 8# catalyst showed excellent stability. At 100 hours on stream, the selectivities to acrylic acid and acetic acid were well maintained at 80% and 11%, respectively. Considering the fast deactivation of the catalysts in direct glycerol oxidehydration to acrylic acid of the prior art, the performance of the current catalytic system is outstanding in terms of the high activity, selectivity, and stability.

In conclusion, the inventors have demonstrated a highly efficient protocol for the production of acrylic acid from glycerol. The process involved glycerol deoxydehydration to allyl alcohol in liquid phase and allyl alcohol oxidation to acrylic acid in gas phase. About 84% overall yield of acrylic acid was achieved from glycerol by the two-step reaction. Formic acid (a cheap and green chemical) was used as key reagent in the first step and metal oxides were used as catalyst in the second step. It is noteworthy that both steps can be carried out in the continuous manner, and this is very favorable for the practical application of the process. Compared with the fast catalyst deactivation in the process of glycerol oxidehydration to acrylic acid (of the prior art), the current catalytic system is highly stable and 80% yield to acrylic acid was maintained for 100 hours. Hence, the current application provides a new and prominent method for the production of acrylic acid from bio-renewable glycerol.

INDUSTRIAL APPLICABILITY

The disclosed method may enable the production of arylic acid from glycerol at high yields, high selectivities to acrylic acid and may be highly stable. The disclosed method made up of the two steps of deoxydehydration and oxidation may be carried out in a continuous manner. The metal oxide catalysts used in the disclosed method may not suffer from catalyst deactivation.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method for synthesizing an alkenoic acid comprising the step of oxidizing an alkenyl alcohol in the presence of a metal oxide catalyst to form said alkenoic acid, wherein said metal oxide catalyst has the formula $Mo_xV_yW_mO_d$
wherein
x is 8;
y is 2;
m is 1; and
d is calculated based on the formula $3x+2y+3m$.

2. The method of claim 1, further comprising, before said oxidizing step, the step of deoxydehydrating a polyol to obtain said alkenyl alcohol.

3. The method of claim 2, wherein said polyol is a triol, tetraol, pentanol or hexanol.

4. The method of claim 3, wherein said polyol is selected from the group consisting of glycerol, 2-methyl-1,2,3-propanetriol, 1,2,3-butanetriol, 2-methyl-1,2,3-butanetriol, 2-methyl-1,2,3,4-butanetetraol, 1,2,3-pentanetriol, 1,2,3-hexanetriol, xylitol, sorbitol, arabinitol, ribitol, mannitol, galactitol, iditol, erythritol, threitol and mixtures thereof.

5. The method of claim 1, wherein said alkenyl alcohol is a 2-alkenyl alcohol.

6. The method of claim 5, wherein said 2-alkenyl alcohol is selected from the group consisting of allyl alcohol, 2-buten-1-ol, 2-hexen-1-ol, 2-penten-1,4,5-triol, 2,4-hexadien-1,6-diol, 2-hexene-1,4,5,6-tetraol, 2-methyl-2-butenol, 2-butene-1,4-diol, 2-methyl-2-butene-1,4-diol, methallyl alcohol, and 2-chloroallyl alcohol.

7. The method of claim 1, wherein said alkenoic acid is a linear or branched monocarboxylic or dicarboxylic acid having three to six carbon atoms.

8. The method of claim 7, wherein said alkenoic acid is selected from the group consisting of acrylic acid, methacrylic acid, maleic acid, fumaric acid, 4-hydroxy-2-butenoic acid, 2-hydroxy-3-pentendioic acid, 4,5-dihydroxy-2-pentenoic acid, 2,5-dihydroxy-3-pentenoic acid, crotonic acid, citraconic acid, mesaconic acid, angelic acid, tiglic acid, 4,5,6-trihydroxy-2-hexenoic acid, 2,3,5-trihydroxy-4-hexenoic acid and 4,5-dihydroxy-2-hexenedionic acid.

9. The method of claim 1, wherein the metal oxide catalyst is provided on a support.

10. The method of claim 1, wherein the amount of metal oxide catalyst used in the oxidizing step is in the range of 10 mg to 500 mg.

11. The method of claim 1, wherein the oxidizing step is undertaken at a temperature above 300° C.

12. The method of claim 1, wherein the oxidizing step is undertaken at an oxygen content of about 5 vol % to about 20 vol %.

13. The method of claim 2, wherein the deoxydehydrating step is undertaken in the presence of a carboxylic acid.

14. The method of claim 2, wherein the deoxydehydrating step is undertaken at a temperature in the range of about 200° C. to about 280° C.

15. The method of claim 2, wherein the deoxydehydrating step is undertaken in an inert gas atmosphere or in air.

16. The method of claim 13, wherein the carboxylic acid is present at a molar ratio in the range of about 1:1 to about 3.0:1 (carboxylic acid:polyol).

17. A method for synthesizing an alkenoic acid from a polyol comprising the steps of:
(a) deoxydehydrating the polyol in the presence of a carboxylic acid to form an alkenyl alcohol; and
(b) oxidizing the alkenyl alcohol in the presence of a metal oxide catalyst to form the alkenoic acid, wherein said metal oxide catalyst has the formula $Mo_xV_yW_mO_d$
wherein
x is 8;
y is 2;
m is 1; and
d is calculated based on the formula $3x+2y+3m$.

* * * * *